US009259288B2

(12) United States Patent
Horton

(10) Patent No.: US 9,259,288 B2
(45) Date of Patent: Feb. 16, 2016

(54) APPARATUS AND SYSTEM FOR PERFORMING SURGERY

(71) Applicant: COVIDIEN LP, Mansfield, MA (US)

(72) Inventor: Kenneth W. Horton, South Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 330 days.

(21) Appl. No.: 13/768,520

(22) Filed: Feb. 15, 2013

(65) Prior Publication Data

US 2013/0158360 A1    Jun. 20, 2013

Related U.S. Application Data

(63) Continuation of application No. 12/754,641, filed on Apr. 6, 2010, now abandoned.

(60) Provisional application No. 61/169,017, filed on Apr. 14, 2009.

(51) Int. Cl.
| | | |
|---|---|---|
| *A61B 1/32* | (2006.01) | |
| *A61B 19/00* | (2006.01) | |
| *A61B 1/06* | (2006.01) | |
| *A61B 17/00* | (2006.01) | |
| *A61B 17/34* | (2006.01) | |

(52) U.S. Cl.
CPC ............... *A61B 19/5202* (2013.01); *A61B 1/06* (2013.01); *A61B 17/00234* (2013.01); *A61B 17/34* (2013.01); *A61B 2017/00278* (2013.01); *A61B 2017/00283* (2013.01)

(58) Field of Classification Search
CPC ........... A61B 19/5202; A61B 19/5212; A61B 19/52; A61B 2019/5204; A61B 2019/5206; A61B 2019/521; A61B 2019/5214; A61B 2019/5217; A61B 2019/5219; A61B 2019/5221; A61B 2019/2253; A61B 2019/2257; A61B 2017/00876; A61B 2017/00283
USPC .................................................. 600/245, 249
See application file for complete search history.

(56) References Cited

U.S. PATENT DOCUMENTS

| | | | |
|---|---|---|---|
| 3,924,631 | A | 12/1975 | Mancusi, Jr. |
| 4,402,314 | A | 9/1983 | Goode |
| 4,898,175 | A | 2/1990 | Noguchi |
| 5,032,024 | A | 7/1991 | Cope |
| 5,423,321 | A | 6/1995 | Fontenot |
| 5,425,367 | A | 6/1995 | Shapiro et al. |
| 5,678,556 | A | 10/1997 | Maki et al. |
| 5,810,719 | A | 9/1998 | Toida |
| 5,823,942 | A | 10/1998 | Toida |
| 5,879,306 | A | 3/1999 | Fontenot et al. |
| 5,906,579 | A | 5/1999 | Salm et al. |
| 5,907,395 | A | 5/1999 | Schulz et al. |
| 6,081,741 | A | 6/2000 | Hollis |
| 6,253,097 | B1 | 6/2001 | Aronow et al. |
| 6,256,522 | B1 | 7/2001 | Schultz |

(Continued)

*Primary Examiner* — Mary Hoffman

(57) ABSTRACT

An illumination system configured to light an anatomical location of a patient is provided. The illumination system includes an interior illumination device positionable and movable within a body cavity of a patient. The interior illumination device is configured to provide a light having a wavelength that is visible to a clinician. The illumination system includes an exterior illumination device operatively coupled to the interior illumination device and positionable and movable about an exterior of a patient. The exterior illumination device is configured to provide a light having a wavelength that is visible to a clinician.

12 Claims, 3 Drawing Sheets

(56) References Cited

U.S. PATENT DOCUMENTS

| | | |
|---|---|---|
| 6,311,083 B1 | 10/2001 | Abraham-Fuchs et al. |
| 6,332,089 B1 | 12/2001 | Acker et al. |
| 6,419,626 B1 | 7/2002 | Yoon |
| 6,516,216 B1 | 2/2003 | Fontenot et al. |
| 6,597,941 B2 | 7/2003 | Fontenot et al. |
| 6,671,526 B1 | 12/2003 | Aoyagi et al. |
| 6,685,666 B1 | 2/2004 | Fontenot |
| 6,773,393 B1 | 8/2004 | Taniguchi et al. |
| 6,796,976 B1 | 9/2004 | Chin et al. |
| 6,813,512 B2 | 11/2004 | Aldefeld et al. |
| 6,855,111 B2 | 2/2005 | Yokoi et al. |
| 6,951,536 B2 | 10/2005 | Yokoi et al. |
| RE39,102 E | 5/2006 | Schulz et al. |
| 7,190,991 B2 | 3/2007 | Cable et al. |
| 7,273,056 B2 | 9/2007 | Wilson et al. |
| 7,311,107 B2 | 12/2007 | Harel et al. |
| 7,316,647 B2 | 1/2008 | Kimoto et al. |
| 7,344,587 B2 | 3/2008 | Khan et al. |
| 7,491,956 B2 | 2/2009 | Knoche et al. |
| 7,652,764 B2 | 1/2010 | Herve et al. |
| 7,678,043 B2 | 3/2010 | Gilad |
| 7,678,100 B2 | 3/2010 | Chin et al. |
| 7,871,375 B2 * | 1/2011 | Talieh ............... 600/249 |
| 7,918,708 B2 | 4/2011 | Kowalski |
| 7,993,263 B2 | 8/2011 | Yokoi et al. |
| 8,012,087 B2 | 9/2011 | Tenger et al. |
| 8,126,524 B2 | 2/2012 | Balberg et al. |
| 8,177,712 B2 | 5/2012 | Fujimori et al. |
| 8,246,537 B2 | 8/2012 | Fujimori et al. |
| 2003/0095781 A1 * | 5/2003 | Williams ............... 385/146 |
| 2004/0138552 A1 * | 7/2004 | Harel et al. ............... 600/407 |
| 2005/0182318 A1 * | 8/2005 | Kaji et al. ............... 600/424 |
| 2006/0217597 A1 * | 9/2006 | Vayser et al. ............... 600/249 |
| 2006/0229508 A1 | 10/2006 | Kermani et al. |
| 2006/0264761 A1 | 11/2006 | Knoche et al. |
| 2007/0142708 A1 | 6/2007 | Yokoi et al. |
| 2008/0033257 A1 | 2/2008 | Yokoi et al. |
| 2008/0051665 A1 | 2/2008 | Xu et al. |
| 2008/0188794 A1 * | 8/2008 | Oritz et al. ............... 604/48 |
| 2010/0113872 A1 * | 5/2010 | Asada et al. ............... 600/102 |
| 2010/0286487 A1 * | 11/2010 | Van Lue ............... 600/249 |
| 2012/0065627 A1 * | 3/2012 | Ghabrial et al. ............... 606/1 |
| 2012/0203069 A1 | 8/2012 | Hannaford et al. |
| 2014/0012139 A1 * | 1/2014 | Sharonov ............... 600/476 |
| 2014/0358162 A1 * | 12/2014 | Valdastri et al. ............... 606/130 |

\* cited by examiner

APPARATUS AND SYSTEM FOR PERFORMING SURGERY

CROSS-REFERENCE TO RELATED APPLICATIONS

This application is a continuation of and claims the benefit of and priority to U.S. patent application Ser. No. 12/754,641, filed Apr. 6, 2010, which claims the benefit of and priority to U.S. Provisional Patent Application No. 61/169,017, filed Apr. 14, 2009, the entire disclosures of which are incorporated by reference herein.

BACKGROUND

1. Technical Field

The present disclosure relates to an apparatus and system for performing surgery and, more particularly, to an apparatus and system that includes an illumination device configured to illuminate various anatomical locations of a patient.

2. Related Art

Without limiting the scope of the present disclosure, its background is described herein with respect to surgical procedures, and in particular, laparoscopy and transluminal and endoluminal surgery, e.g., Natural Orifice Transluminal Endoscopic Surgery (NOTES).

Compared with open surgery, laparoscopy results in significantly less pain, faster convalescence and less morbidity. NOTES, an even less invasive surgical approach, is likely to achieve similar results. However, eye-hand dissociation, a two-dimensional field-of-view and instrumentation with limited degrees of freedom contribute to a steep learning curve and demanding dexterity requirements for many laparoscopic and endoscopic procedures. A limitation of laparoscopic and endoscopic procedures is the fixed working envelope surrounding each trocar, often necessitating placement of multiple ports to accommodate changes in position of the instruments or laparoscope to improve visibility and efficiency. The placement of additional working ports contributes to postoperative pain and carries a small risk of bleeding or adjacent organ damage. Another limitation of laparoscopic and endoscopic procedures is that the images often appear "upside-down" and/or "backward" due to the flexible rather than rigid scope typically employed by a clinician during the laparoscopic and endoscopic procedures, which, may result in a clinician becoming disoriented during the laparoscopic and endoscopic procedures.

Therefore, it may prove advantageous to provide an illumination guidance apparatus and system configured for use with a surgical space in a minimally invasive surgical procedure while avoiding any one or combination of the aforementioned limitations.

SUMMARY

The present disclosure provides an illumination system configured to light an anatomical location of a patient. The illumination system includes an interior illumination device positionable and movable within a body cavity of a patient. The interior illumination device is configured to provide a light having a wavelength that is visible to a clinician. The illumination system includes an exterior illumination device operatively coupled to the interior illumination device and positionable and movable about an exterior of a patient. The exterior illumination device is configured to provide a light having a wavelength that is visible to a clinician.

The present disclosure also provides an illumination apparatus configured to light an anatomical location of a patient. The illumination apparatus includes a proximal end configured for manipulation by a clinician. The illumination apparatus includes an elongate tubular portion extending distally from the proximal end of the illumination apparatus. An exterior illumination device is fixedly positionable on an outer abdominal wall of a patient and disposed at the proximal end of the illumination apparatus. The exterior illumination device is configured to provide a light having a wavelength that is visible to a clinician. An interior illumination device is disposed at a distal end of the illumination apparatus and operatively coupled to the exterior illumination device. The interior illumination device is also configured to provide a light having a wavelength that is visible to a clinician.

BRIEF DESCRIPTION OF THE DRAWINGS

Various embodiments of the present disclosure are described herein with reference to the drawings wherein.

DETAILED DESCRIPTION

An illumination system and apparatus in accordance with the teaching of the present disclosure may be used by a clinician to form a plurality of markers or beacons that are configured to light an anatomical location of a patient and facilitate a clinician in navigating within an anatomical location of a patient during a surgical procedure.

Figure 1:
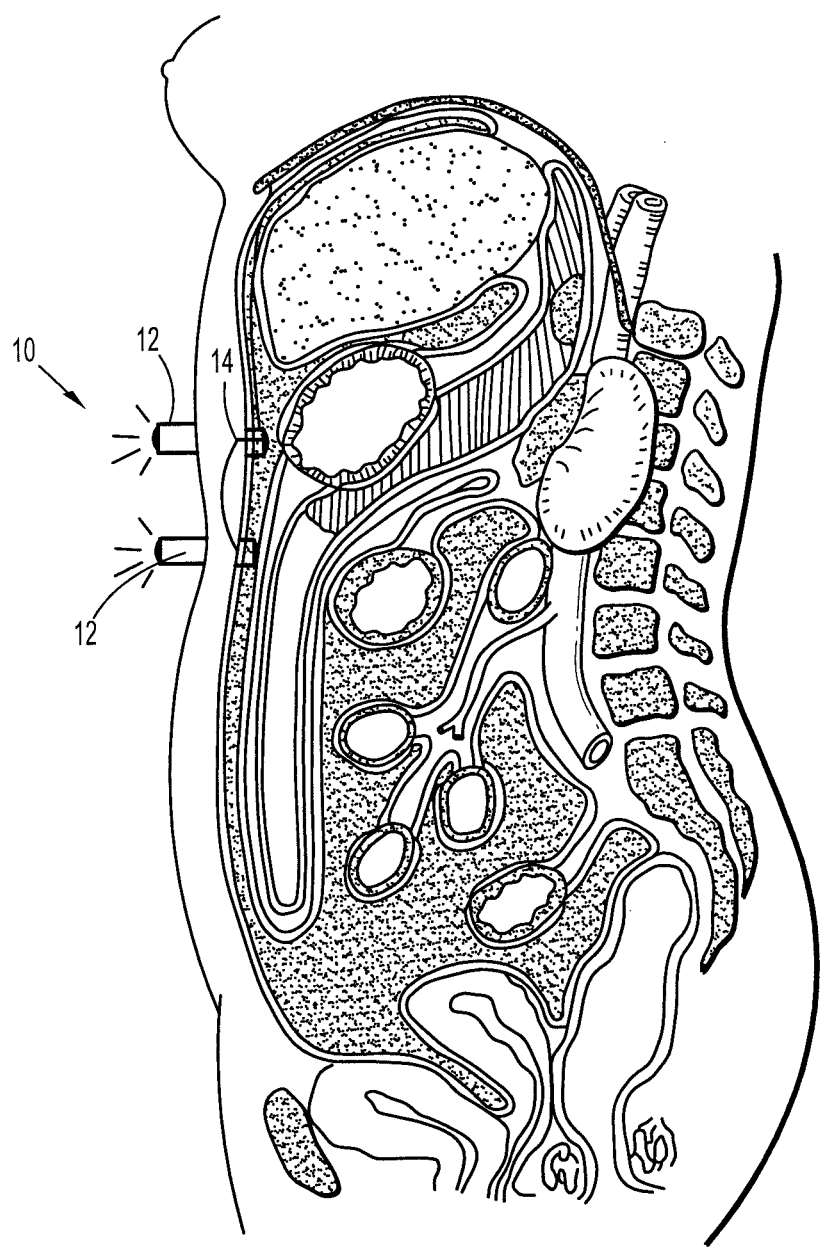
FIG. 1 illustrates an illumination system according to an embodiment of the present disclosure.
Figure 2:
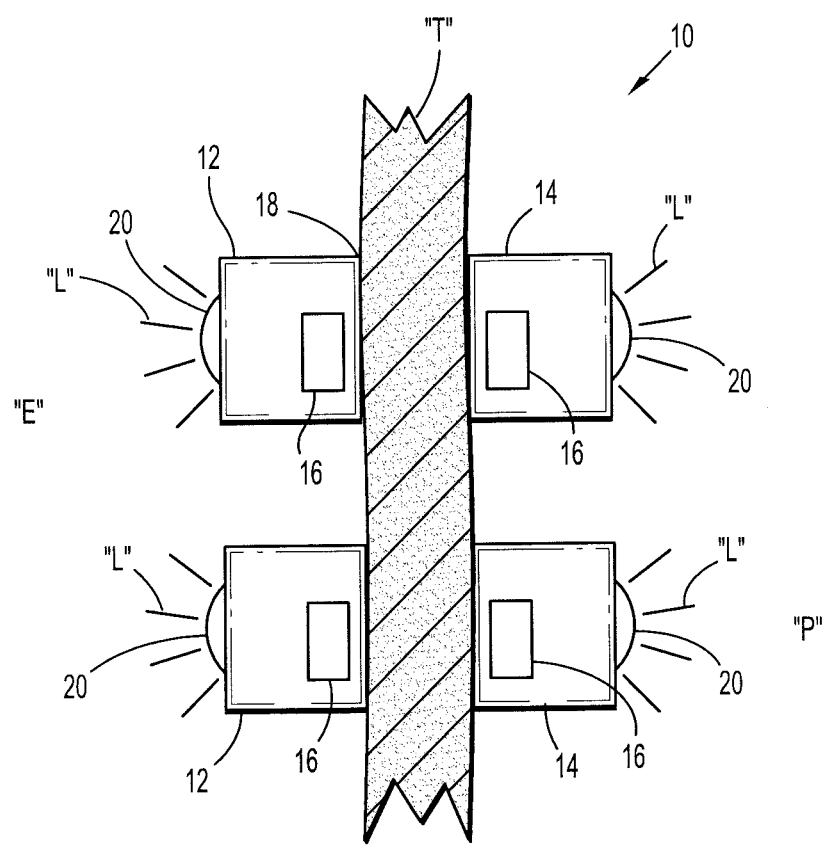
FIG. 2 illustrates a side view of the illumination system depicted in FIG. 1.

Referring to FIGS. 1 and 2, and initially with reference to FIG. 1, an illumination system 10 according to an embodiment of the present disclosure is shown. In the embodiment illustrated in FIGS. 1 and 2, illumination system 10 includes a plurality of markers in the form of illumination devices 12 and 14. Illumination devices 12 and 14 are selectively positionable on a patient and configured to emit light that is visible to a clinician.

In the embodiments illustrated in FIGS. 1 and 2, illumination system 10 includes an exterior illumination device 12 positionable on an exterior "E" of a patient (e.g., skin of a patient), and an interior illumination device 14 positionable within an interior of a patient (e.g., peritoneal cavity "P" of a patient). In the embodiments illustrated in FIGS. 1 and 2, illumination devices 12 and 14 are coupled or attracted to each other by way of a magnetic field produced by one or more suitable devices (e.g., permanent magnets, electromagnets, or other suitable devices or structures configured to produce a magnetic field) associated with one or both of the illumination devices 12 and 14. For illustrated purposes, the magnetic field is assumed to be produced by way of a permanent magnet 16. Magnet 16 is attached, connected, or operatively disposed on one or both of illumination devices 12 and 14. In the embodiments illustrated in FIGS. 1 and 2, magnet 16 provides a magnetic field that is used to operatively couple the exterior and interior illumination devices 12 and 14, respectively, to each other. While the exterior and interior devices 12 and 14 have been described herein as each including a magnet 16, it is within the purview of the present disclosure to have one of the illumination devices include a magnet 16 and the other illumination devices include or be made from a ferromagnetic and/or paramagnetic material that is influenced by a magnetic field.

Exterior illumination device 12 may have any suitable shape. Exterior illumination device 12 may be formed from any suitable material. In the embodiments, illustrated in FIGS. 1 and 2, exterior illumination device 12 includes a base 18 that is configured to rest on an exterior surface of a patient. Exterior illumination device 12 includes one or more suitable light emitting elements 20 (e.g., bulbs, LEDs, etc.) configured to emit light "L" in the visible light spectrum. In an embodiment, light emitting element 20 is configured to emit light "L" of varying intensity. That is, light "L" may change from a dim light to a bright light and/or vice-versa. Light emitting element 20 may be configured to generate a continuous or intermittent light "L". Light emitting element 20 may be configured to emit different colors of light "L".

Interior illumination device 14 is substantially similar to exterior illumination device 12. Interior illumination device 14 includes a light emitting element 20, a base 18, and one or more magnets 16 each of which function as previously described herein. As noted above, interior element 14 is configured for placement within the peritoneal cavity "P" of a patient and, as such, interior illumination device 14 is formed from any suitable bio-compatible material. Alternatively, interior illumination device 14 may be encased within a bio-compatible material. Interior illumination device 14 may be introduced into the peritoneal cavity by any suitable surgical procedures and/or methods (e.g., transluminal, endoluminal or laparoscopic surgical procedures). Interior illumination device 14 may include any suitable structure configured to facilitate a user in properly positioning interior illumination device 14 within an interior of a patient.

In embodiments, each of exterior and/or interior illumination devices, 12 and 14, respectively, may be formed from or configured to receive a lubricous material that is configured to facilitate a clinician in moving the exterior and interior illumination devices 12 and 14, when they are coupled to one another and positioned on a patient. More particularly, and in embodiments, each of exterior and interior illumination devices 12 and 14, or portions thereof, may be formed from polytetrafluoroethylene (PTFE) or other suitable material. Alternatively, or in addition thereto, each of exterior and interior illumination devices 12 and 14, or portions thereof, may be configured to receive one or more suitable types of material that is lubricious in nature, such as, for example, lanolin, water, mineral oils, natural oils (e.g., vegetable oils), synthetic oils, etc.

In use, multiple pairs of exterior and interior illumination devices 12 and 14, respectively, may be positioned on and within a patient. More particularly, an exterior illumination device 12 may be positioned on a patient and an interior illumination device 14 may be positioned within an interior of a patient and adjacent to exterior illumination device 12. The magnetic field produced by magnet 16 attracts or couples the exterior and interior illumination devices 12 and 14, respectively to each other. Once the exterior and interior illumination devices 12 and 14 are magnetically coupled to one another, a clinician may move the exterior and interior illumination devices 12 and 14 to a desired location on a patient. After the exterior and interior illumination devices 12, and 14, respectively, have been properly positioned, second, third, fourth, etc. additional pairs of respective exterior and interior illumination devices 12 and 14 may be positioned (see FIGS. 1 and 2). Once properly positioned on a patient, both exterior and interior illumination devices 12 and 14, respectively, emit light "L" of a suitable wavelength. This light "L" provides a clinician with a light path such that a clinician may effectively navigate a surgical instrument within the peritoneal cavity "P" of a patient.

Figure 3:
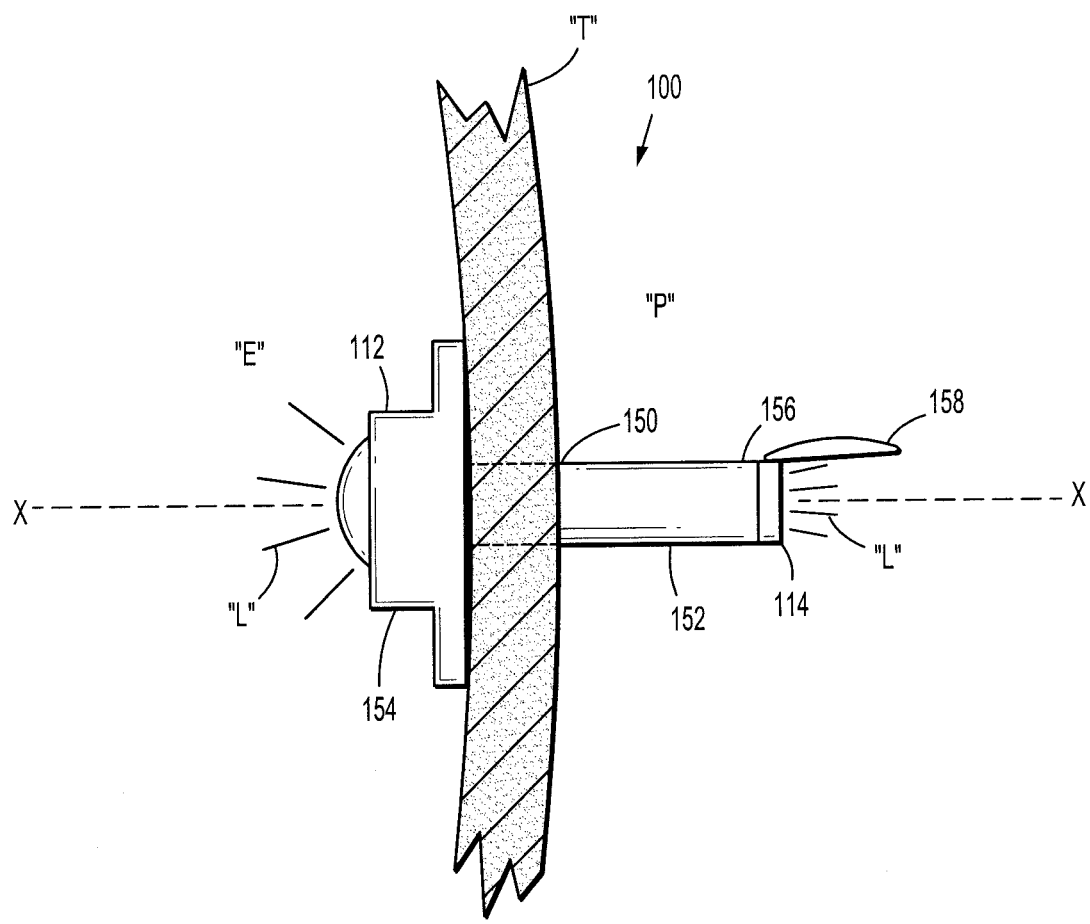
FIG. 3 illustrates an illumination system according to another embodiment of the present disclosure.

FIG. 3 illustrates an illumination apparatus 100 in accordance with an embodiment of the present disclosure. Illumination apparatus 100 is similar to illumination apparatus 10 in that both illumination assemblies 10 and 100 are positionable upon an exterior "E" and interior body cavity of patient and intended to provide a light that is visible to a clinician. Illumination apparatus 100 is different from illumination apparatus 10 in that illumination apparatus 100 is configured to fixedly attach to a patient. With this purpose in mind, illumination apparatus 100 includes exterior and interior illumination devices, 112 and 114, respectively that are operatively coupled to each other by way of one or more suitable structures 150.

By way of example only, illumination apparatus 100 includes a structure 150 that is configured to support and/or house exterior and interior illumination devices, 112 and 114, respectively. In the embodiment illustrated in FIG. 3, structure 150 is in the form of a percutaneous needle 150. Structure 150 includes a proximal end 154 that is configured for manipulation by a clinician. To this end, proximal end 154 may include one or more suitable structures configured to facilitate gripping of the proximal end 154. Proximal end 154 is also configured to support and/or house exterior illumination device 112 such that exterior illumination device can function in a manner previously described herein. A seal and/or clamp apparatus (not shown) may be located at proximal end 154 to support illumination apparatus 100 in a substantially fixed position on a patient.

An elongate tubular portion 152 defining a longitudinal axis "X" therethrough extends distally from proximal end 154. In embodiments, tubular portion 152 may define or include one or more lumens configured to provide a fluid path for one or more suitable insufflation fluids.

Illumination apparatus also includes a distal end 156 that is configured to support and/or house interior illumination device 114. In the embodiment illustrated in FIG. 3 distal end 156 includes a tissue piercing distal tip 158. Alternatively, distal end 154 may have a blunt tip configuration.

In the embodiment illustrated in FIG. 3, each of exterior and interior illumination devices, 112 and 114, respectively are configured to function as previously described herein with respect to the illumination system 10.

In use, distal tip 158 of illumination apparatus 100 may be employed to pierce an outer abdominal wall of a patient such that exterior and interior illumination devices 112 and 114, respectively, may be properly positioned on a patient. Once properly positioned on a patient, both exterior and interior illumination devices 112 and 114, respectively, emit light "L" of a suitable wavelength, such that a clinician may effectively navigate a surgical instrument within an interior of a patient.

From the foregoing and with reference to the various figure drawings, those skilled in the art will appreciate that certain modifications can also be made to the present disclosure without departing from the scope of the same. For example, it is contemplated that a roller or bearing (not shown) may be operatively disposed on or near the base 20 of one or both of the illumination devices 12, 14. The roller or bearing may be configured to facilitate movement of the illumination devices 12, 14 when the illumination devices 12, 14 are in contact with a patient.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for illuminating an anatomical location of a patient comprising:
    positioning a first interior illumination device within a body cavity of a patient;
    positioning a first exterior illumination device about an exterior surface of the patient, the first exterior illumination device moveable independent of the first interior illumination device;
    coupling the first exterior illumination device to the first interior illumination device; and
    moving the first exterior illumination device across the exterior surface of the patient to move the first interior illumination device to a desired location within the body cavity of the patient to illuminate the body cavity.

2. The method according to claim 1, including positioning a second interior illumination device within the body cavity of the patient and a second exterior illumination device about the exterior surface of the patient, the second exterior illumination device configured to couple to one of the first or second interior illumination devices.

3. The method according to claim 1, including providing a light emitting element on each of the first interior and exterior illumination devices.

4. The method according to claim 3, including emitting light in the visible light spectrum, wherein the emitted light is one of continuously and intermittently emitted.

5. The method according to claim 3, including selecting the light emitting element from the group consisting of bulbs and light emitting diodes.

6. The method according to claim 1, including utilizing a surgical procedure selected from the group consisting of a transluminal procedure, endoluminal procedure and laparoscopic procedure to position the first interior illumination device within the body of the patient.

7. The method according to claim 1, including providing at least one of the first interior or exterior illumination devices with at least one magnet configured to magnetically couple the first interior and exterior illumination devices to one another.

8. The method according to claim 1, wherein positioning the first interior illumination device includes positioning the first interior illumination device within a peritoneal cavity of the patient.

9. The method according to claim 1, including forming at least a portion of the first interior or exterior illumination devices from a lubricious material.

10. The method according to claim 9, including selecting the lubricious material from the group consisting polytetrafluoroethylene, lanolin, water, mineral oils, natural oils and synthetic oils.

11. The method according to claim 1, including forming the first interior illumination device from a biocompatible material.

12. The method according to claim 1, including encasing the first interior illumination device in a biocompatible material.

* * * * *